US00PP13843P29

(12) United States Plant Patent
Schräder

(10) Patent No.: US PP13,843 P2
(45) Date of Patent: May 20, 2003

(54) PLECTRANTHUS PLANT NAMED 'SUMCOL 01'

(75) Inventor: Ralf Schräder, Lüdinghausen (DE)

(73) Assignee: Jungpflanzen Grunewald GmbH (DE)

( * ) Notice: Subject to any disclaimer, the term of this patent is extended or adjusted under 35 U.S.C. 154(b) by 0 days.

(21) Appl. No.: 10/053,418

(22) Filed: Nov. 7, 2001

(51) Int. Cl.[7] ..... A01H 5/00

(52) U.S. Cl. ..... Plt./373

(58) Field of Search ..... Plt./373

*Primary Examiner*—Kent Bell
(74) *Attorney, Agent, or Firm*—Webb Ziesenheim Logsdon Orkin & Hanson PC

(57) ABSTRACT

A Plectranthus plant named 'Sumcol 01' particularly characterized by its strong fragrance and compact, rounded shape. The plant has an appealing leaf color. The plant has shown resistance to botrytis, snails, and caterpillars. Animals avoid the present plant because of its strong fragrance.

1 Drawing Sheet

BOTANICAL CLASSIFICATION

Plectranus hybrid.

VARIETAL DENOMINATION

'Sumcol 01'.

BACKGROUND OF THE INVENTION

The present invention comprises a new and distinct cultivar of Plectranthus hybrid known by the varietal name 'Sumcol 01'.

The new cultivar was discovered in a planned breeding program in Lüdinghausen Germany in July 2000 and is from a controlled cross of an unnamed, unpatented female *Plectranthus canina* plant with an unnamed, unpatented male *Plectranthus esculentus* plant. The purpose of the breeding program was to produce a Plectranthus plant with compact growth habit.

The following traits compare the new cultivar from other cultivated plants of this type known to the inventor. The characteristics are described with comparative reference to the cultivar's female and male parents.

1. The female parent grows stronger than 'Sumcol 01' and is in hanging form.
2. 'Sumcol 01' has a stronger fragrance than the female and male parents.
3. 'Sumcol 01' has better leaf color than the female parent.
4. 'Sumcol 01' is more compact than the female and male parents.
5. 'Sumcol 01' has similar leaves to the male parent.
6. The male parent is in the hanging form.

The first asexual reproduction took place at Lüdinghausen, Germany in January 2001 by cuttings. Continued observations from the vegetative cuttings have confirmed that the distinguishing features of the new cultivar remain stable and are retained through successive propagations.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out in Lüdinghausen, Germany of a 12 week old plant, in a 20 cm container. Color references are primarily to The R.H.S. Colour Chart of The Royal Horticultural Society of London except where general terms of ordinary dictionary significance were used.

PLANT

Height: 25 cm.
Width: 30 cm.
Form: Compact, rounded.
Stems:
- *Size.*—21 mm long.
- *Surface texture.*—Fleshy.
- *Color.*—Yellow-Green Group 153A.
- *Diameter.*—8–10 mm.
- *Internode length.*—25–30 mm.

Branches:
- *Surface texture.*—Fleshy.
- *New growth color.*—Yellow-Green Group 145A.
- *Mature growth color.*—Yellow-Green Group 146C.
- *Internode length.*—10.5 mm.

Leaves:
- *Length.*—35 mm.
- *Width.*—33 mm.
- *Surface texture.*—Rippled.
- *Shape.*—Overall: Obovate. Apex: Acute. Base: Rotundate. Margin: Crenate.
- *Color.*—Upper surface: Greyed-Green Group 189A. Lower surface: Greyed-Green Group 191A.
- *Mid-vein.*—Size: 17 mm. Color: Yellow-Green Group 145C. Length: Approximately 30 mm. Width: 1–2 mm.
- *Petioles.*—Length: 12 mm. Diameter: 2–3 mm. Thickness: Moderate. Color: Yellow-Green Group 145C.

Growing conditions: The new cultivar is preferably cultivated in peat soil at a pH between 5.5 and 6.0. The natural flowering period is summer. Freezing temperatures are fatal to the new cultivar.

Time it takes to produce a finished plant:
*In a 10–11 cm container.*—8 weeks.
*In a 20–21 cm container.*—12 weeks.
Disease resistance: Botrytis; snails; caterpillars.
Other features: Cats and dogs avoid the present cultivar because of its strong fragrance.

INFLORESCENCE

Type: Paniculate.
Length: 80 mm.
Diameter: 16 mm.
Peduncles:
*Color.*—Yellow-Green Group 145A.
*Length.*—80 mm.
*Diameter.*—12–15 mm.

BUDS

Shape: Cylinder-like with spikes.
Length: 40 mm.
Diameter: 15–20 mm.
Color: Yellow-Green Group 147A.

FLOWERS

Average number of blooms per cluster: 20 to 30.
Form: Single to bilabiate.
Color when opening begins:
*Upper surface.*—Violet-Blue Group 97B.
*Lower surface.*—Violet-Blue Group 97B.
Color when blooming:
*Upper surface.*—Violet-Blue Group 97B.
*Lower surface.*—Violet-Blue Group 97B.
Color at end of blooming:
*Upper surface.*—Violet-Blue Group 97B.
*Lower surface.*—Violet-Blue Group 97B.
Fragrance: Unpleasant.
Petals:
*Form.*—Ovial and labiate.
*Number.*—Two.
*Length.*—22 mm.
*Width.*—6 mm.
*Apex.*—Acuminate.
*Base.*—Cordate.
*Margin.*—Entire.
*Lasting quality.*—5 to 8 days from opening to end of life.
Sepals:
*Number.*—1.
*Length.*—12 mm.
*Width.*—8 mm.
*Shape.*—Lanceolate.
*Apex.*—Pointed.
*Margin.*—Entire.
*Color* (*young sepal*).—Upper surface: Violet Group N88C. Lower surface: Violet Group 85D.

REPRODUCTIVE ORGANS

Sexual characteristics: Bisexual.
Pistils:
*Number.*—One.
*Ovaries.*—Shape: 4 small ovals in cruciform. Length: 1 mm. Width: 1 mm. Color: Yellow-Green Group 153D.
*Style.*—Length: 20–23 mm. Color: Violet-Blue Group N89B.
Stamens:
*Number.*—Four.
*Length.*—20 mm.
*Shape.*—Round; tube.
*Color.*—Violet-Blue Group N89B.
*Pollen.*—Amount: Some. Color: Violet-Blue Group N89B.

FRUIT

Maturity date: 21 days from crossing until fruit produced.
Length: Approximately 0.5–0.8 mm.
Width: Approximately 0.5–0.8 mm.
Shape: Round; uniform.
Color: Brown Group 200A.
Flesh texture: Hard.

I claim:

1. A new and distinct variety of Plectranthus plant as herein shown and described, particularly characterized by its strong fragrance and compact, rounded shape.

* * * * *

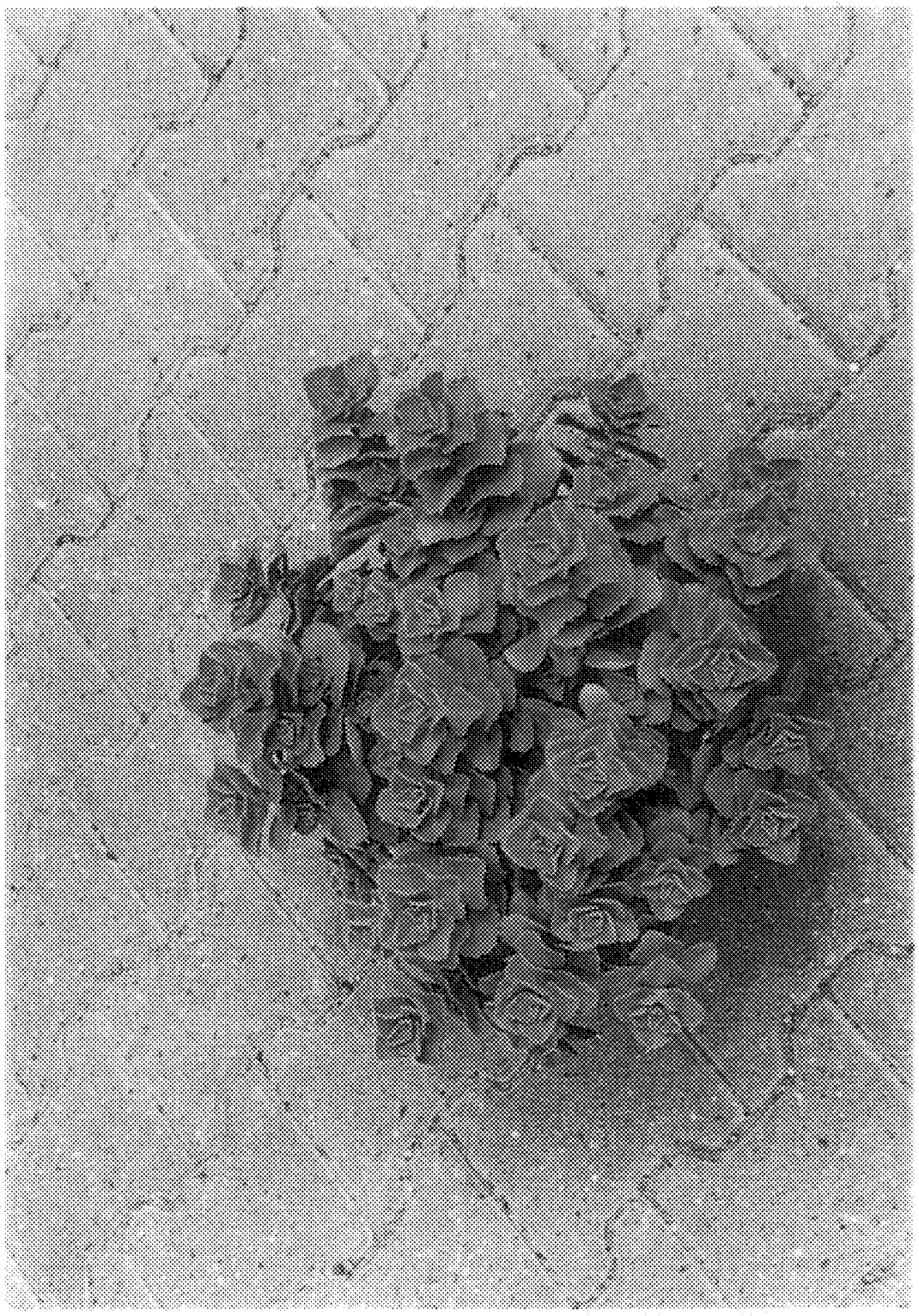

UNITED STATES PATENT AND TRADEMARK OFFICE

CERTIFICATE OF CORRECTION

PATENT NO. : PP 13,843 P2
DATED : May 20, 2003
INVENTOR(S) : Ralf Schräder

It is certified that error appears in the above-identified patent and that said Letters Patent is hereby corrected as shown below:

Column 1,
Line 2, “Plectranus hybrid” should read -- Plectranthus hybrid --.

Signed and Sealed this

Sixteenth Day of September, 2003

JAMES E. ROGAN
*Director of the United States Patent and Trademark Office*